(12) United States Patent
Rogers

(10) Patent No.: US 10,159,473 B2
(45) Date of Patent: Dec. 25, 2018

(54) ACTUATION CABLE HAVING MULTIPLE FRICTION CHARACTERISTICS

(71) Applicant: Intuitive Surgical Operations, Inc., Sunnyvale, CA (US)

(72) Inventor: Theodore W. Rogers, Alameda, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 14/929,256

(22) Filed: Oct. 31, 2015

(65) Prior Publication Data

US 2016/0051331 A1 Feb. 25, 2016

Related U.S. Application Data

(62) Division of application No. 12/946,040, filed on Nov. 15, 2010, now Pat. No. 9,198,729.

(51) Int. Cl.
*A61B 17/00* (2006.01)
*A61B 34/30* (2016.01)
*A61B 34/00* (2016.01)

(52) U.S. Cl.
CPC ........ *A61B 17/00234* (2013.01); *A61B 34/30* (2016.02); *A61B 34/71* (2016.02); *A61B 2017/00323* (2013.01); *A61B 2017/00477* (2013.01); *A61B 2017/00845* (2013.01); *A61B 2017/00858* (2013.01); *A61B 2034/302* (2016.02); *A61B 2034/715* (2016.02); *Y10T 29/49* (2015.01)

(58) Field of Classification Search
CPC ... A61B 34/30; A61B 34/71; A61B 17/00234; A61B 2034/715; A61B 2017/00853; A61B 2017/00858
USPC .......................................................... 606/1
See application file for complete search history.

(56) References Cited

U.S. PATENT DOCUMENTS 5,133,360 A * 7/1992 Spears ............... A61B 10/0266
600/567
5,234,425 A * 8/1993 Fogarty ................ A61B 17/221
606/1
5,797,900 A 8/1998 Madhani et al.
(Continued)

FOREIGN PATENT DOCUMENTS

WO WO-9950721 A1 10/1999
WO WO-2006053198 A2 5/2006
WO WO-2007096950 A1 8/2007

OTHER PUBLICATIONS

PCT/US11/058386 International Search Report and Written Opinion of the International Searching Authority, dated Mar. 23, 2012, 22 pages.

(Continued)

*Primary Examiner* — John R Downey

(57) ABSTRACT

A surgical device includes a first cable portion that engages a first component such that a first friction exists between the first cable portion and the first component. The surgical device includes a second cable portion having a first end operatively coupled to a first end of the first cable portion. The second cable portion engages a second component such that a second friction exists between the second cable portion and the second component, such that the second friction is greater than the first friction.

15 Claims, 4 Drawing Sheets

(56) References Cited

U.S. PATENT DOCUMENTS

| | | | |
|---|---|---|---|
| 6,450,948 B1* | 9/2002 | Matsuura | A61B 1/0055 600/139 |
| 2001/0047124 A1 | 11/2001 | Yamamoto | |
| 2002/0133178 A1* | 9/2002 | Muramatsu | A61B 17/1285 606/142 |
| 2003/0085004 A1* | 5/2003 | Witherell | D04C 1/12 160/330 |
| 2004/0044350 A1* | 3/2004 | Martin | A61B 50/30 606/139 |
| 2005/0043718 A1* | 2/2005 | Madhani | A61B 19/2203 606/1 |
| 2006/0052664 A1 | 3/2006 | Julian et al. | |
| 2006/0079884 A1* | 4/2006 | Manzo | A61B 18/1442 606/41 |
| 2006/0085022 A1* | 4/2006 | Hayes | A61M 25/104 606/192 |
| 2006/0258908 A1 | 11/2006 | Stefanchik et al. | |
| 2008/0051631 A1 | 2/2008 | Dejima et al. | |
| 2008/0287963 A1 | 11/2008 | Rogers et al. | |
| 2009/0088774 A1 | 4/2009 | Swarup et al. | |
| 2009/0112230 A1 | 4/2009 | Jinno | |
| 2010/0011901 A1 | 1/2010 | Burbank | |
| 2010/0082041 A1 | 4/2010 | Prisco | |
| 2010/0094392 A1 | 4/2010 | Nguyen et al. | |
| 2010/0168721 A1 | 7/2010 | Rogers et al. | |
| 2010/0233146 A1 | 9/2010 | McDaniel | |
| 2012/0123200 A1 | 5/2012 | Rogers | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ACTUATION CABLE HAVING MULTIPLE FRICTION CHARACTERISTICS

This application is a divisional of U.S. patent application Ser. No. 12/946,040, filed Nov. 15, 2010, which is incorporated by reference in its entirety.

BACKGROUND

Robotically controlled instruments are often used in minimally invasive surgical procedures. An existing architecture for instruments in a surgical system includes an end effector or tool such as forceps, a scalpel, scissors, a wire loop, or a cauterizing instrument mounted at the distal end of an extension, which may also be referred to herein as the main tube of the instrument. During a surgical procedure, the end effector and the distal end of the main tube can be inserted through a small incision or a natural orifice of a patient to position the end effector at a work site within the body of the patient. Tendons, which can be cables or similar structures, extend through the main tube of the instrument and connect the end effector to a transmission and actuation mechanism, which may be referred to herein as a backend mechanism. For robotic operation of the surgical instrument, the backend mechanism at the proximal end of the instrument is motor driven to pull on the tendons and thereby move or otherwise operate the end effector. A computing system may be used to provide a user interface for a surgeon or other user to control the instrument.

Certain robotically controlled surgical instruments have flexible main tubes that are able to bend as necessary to follow a natural lumen, such as a portion of the digestive tract of a patient or for insertion through a curved guide tube that provides an improved approach direction to the surgical site when compared to a straight approach. Whether inserted directly or through a guide, the main tube of a flexible surgical instrument will generally have multiple bends at locations that may vary during a surgical procedure and may vary from one procedure to another. At these bends, the tendons running through the instrument may rub against the inside wall of the main tube of the instrument and against each other, and friction generated due to these bends can increase the forces required to move the tendons to operate the end effector at the distal end of the main tube. Additionally, these frictional forces tend to be higher at zero velocity that at low (e.g., non-zero) velocities, resulting in what is commonly called "stick-slip motion" (and sometimes referred to as "stiction") in response to changes in tendon load. This stick-slip motion makes smooth robotic control of small movements of the end effector difficult to achieve. The large friction also makes construction of small-diameter flexible surgical instruments more difficult because mechanical structures must be designed to be robust enough to withstand the large forces applied.

In many applications, it is desirable to provide actuation cables for controlling the end effector that have minimal friction to reduce the negative impacts of friction on control of the end effector. However, in capstan drives that use friction to retain a driven cable, it is desirable to provide an interface between the capstan surface and the cable that provides a relatively high friction to maintain the coupling between the cable and the capstan surface. Existing systems typically address one of the following two requirements. Using a low-friction cable reduces the negative impacts of friction on the control of the end effector, but reduces the force that can be applied by the capstan due to slippage of the low-friction cable. Alternatively, using a high-friction cable impedes the control of the end effector, but increases the force that can be applied by the capstan due to reduced slippage of the high-friction cable.

Accordingly, instruments are desired that provide a cable offering sufficiently low friction to enable control of an end effector as well as significant friction between the cable and a capstan surface to properly drive the cable.

BRIEF DESCRIPTION OF THE DRAWINGS

Throughout the description, similar reference numbers may be used to identify similar elements.

DETAILED DESCRIPTION

The systems and methods described herein relate to surgical instruments having a cable, an end effector and a backend mechanism to operate the end effector via the cable. In a described embodiment, the cable is formed using two different materials having different friction characteristics. A first cable portion is connected to the end effector and has low friction properties that provide desirable control of the end effector. A second cable portion is connected to the backend mechanism and has high friction properties that permit the application of significant force to the cable by the backend mechanism. In particular, the second cable provides high friction characteristics when engaged with the surface of a drive mechanism, such as a capstan. Many aspects and embodiments are described with reference to a "cable" or a "cable portion". It should be understood, however, that a cable is representative of a "tension element" or "tendon" that is capable of transmitting a pulling force, and such components may be various cables, wires, rods, fibers, threads, and the like. Persons having ordinary skill in the art will understand that such tension elements/tendons in some instances may also be capable of transmitting a pushing force.

Figure 1:
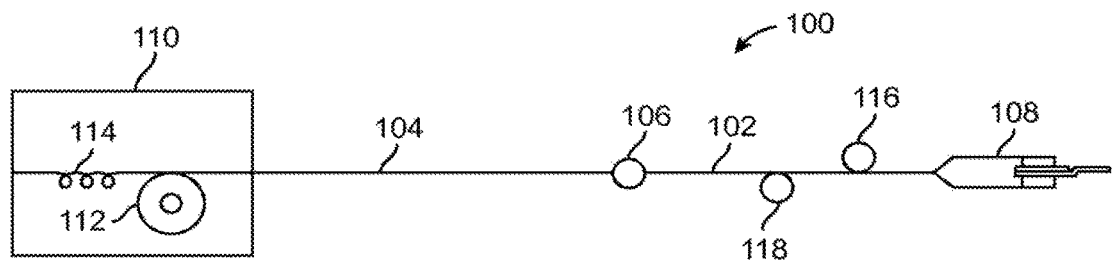
FIG. 1 depicts a surgical instrument in accordance with an embodiment of the invention that includes a cable having two different friction characteristics.

FIG. 1 depicts a surgical instrument 100 in accordance with an embodiment of the invention that includes a cable having two different friction characteristics. Surgical instrument 100 includes a lengthwise first cable portion 102 having low friction properties and a second lengthwise cable portion 104 having high friction properties when engaging a surface of a drive mechanism. In a particular embodiment, cable portion 102 is manufactured using a synthetic polymer, such as high density polyethylene (HDPE). In a specific implementation, cable portion 102 is manufactured using Dyneema®. In the described embodiment, cable portion 104 is manufactured using a different synthetic material having a higher coefficient of friction than the material used for cable portion 102. Example materials for cable portion 104 include an aramid polymer (such as Kevlar®) or PBO (poly(p-phenylene-2,6-benzobisoxazole)).

A coupling element 106 operatively couples cable portion 102 and cable portion 104. Coupling element 106 is any type of coupling mechanism that securely joins the two lengthwise cable portions 102 and 104 end to end. Examples of coupling element 106 include a thimble, an eye, a crimp element, and the like. In alternate embodiments, cable portion 102 is operatively coupled to cable portion 104 by splicing the two cable portions together or braiding/weaving the two cable portions to one another. In other embodiments, cable portion 102 is operatively coupled to cable portion 104 using a knot or similar method of securing the two cable portions to each other.

In one aspect, the distal end of cable portion 102 is connected to a distal component of the instrument, such as distal link or a surgical end effector 108, which can perform various procedures, such as cutting, removal or destruction of tissue, insertion of medical devices, cauterization, vessel sealing, suturing, and the like. Many aspects and embodiments are described in terms of an end effector, and it should be understood that such an end effector is representative of various surgical instrument distal components, such as links in a kinematic chain, wrist mechanisms, end effectors, and the like. In the embodiment of FIG. 1, the low friction properties of cable portion 102 provide desirable control of the end effector by generally avoiding stick-slip motion. In a particular implementation, cable portion 102 includes a lubricated tendon that passes through a sheath, as discussed below with respect to FIG. 9.

In a highly articulated flexible instrument, the total aggregate friction of all of the bends, typically referred to as capstan friction, also greatly degrades the performance of the instrument and is typically approximated as an exponential function of the product of the coefficient of friction and the total angle of wrap. Such capstan friction may result from the cable being routed through one or more guide channels, such as a fairlead, in jointed distal links or past one or more pulleys or so that the cable follows a tortuous path to its termination point. In a particular embodiment, the distal cable portion 102 has both a static coefficient of friction less than or equal to its dynamic coefficient of friction and a sufficiently low dynamic coefficient of friction to allow effective force transmission. As shown in FIG. 1, two components 116 and 118 interact with cable portion 102, generating friction as a result of that interaction. In various embodiments, components 116 and 118 are drive mechanisms, capstans, pulleys, guide channels or other mechanisms that operatively interact with cable portion 102.

The proximal end of cable portion 104 is connected to a backend mechanism 110, which includes a capstan 112 and a tension spring 114. Cable portion 104 wraps around capstan 112 and is held in place by the friction between the surface of cable portion 104 and the surface of capstan 112. The tension spring 114 maintains tension on cable portion 104. In the described embodiment, capstan 112 is a powered capstan, as discussed below with respect to FIGS. 7A and 7B. In alternate embodiments, capstan 112 is replaced with any type of drive mechanism, friction drive or other driving mechanism that uses friction.

A particular implementation of surgical instrument 100 includes a single backend mechanism 110 having multiple capstans 112 connected to multiple cable portions 104, which are coupled to multiple cable portions 102 and corresponding multiple end effectors 108. In this implementation, multiple cable portions 102 are individually sheathed, then bundled and routed through a single main tube. Aspects of this capstan and cable combination are disclosed in U.S. patent application Ser. No. 12/286,644 (filed Sep. 30, 2008; entitled "Passive Preload and Capstan Drive for Surgical Instruments"; published as U.S. Patent Application Pub. No. US 2010/0082041 A1), which is incorporated herein by reference.

As discussed below, certain embodiments of cable portion 102 use a tendon routed through a sheath such that a lubricant is located between the tendon and the sheath. The lubricant maintains a low friction in the cable portion 102, which is desirable for control of the end effector. However, such lubrication of cable portion 104 is not desirable due to a potential of reduced friction between the cable and capstan 112 surface. In certain embodiments, coupling element 106 between cable portions 102 and 104 helps maintain the proper operation of surgical instrument 100 by isolating the lubricant in cable portion 102, where it is desirable to operation of the surgical instrument.

Figure 2:
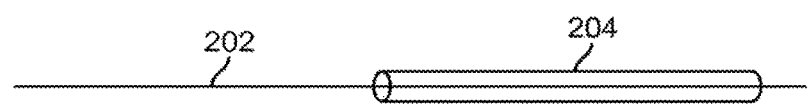
FIG. 2 depicts a cable in accordance with an embodiment of the invention partially covered by a lower friction material.

FIG. 2 depicts a cable 202 partially covered by a lower friction material 204 (also referred to as a "covering material") in accordance with an embodiment of the invention. In this embodiment, cable 202 has high friction characteristics (as desired when interacting with a capstan) and material 204 has a lower friction characteristic (as desired when operating a surgical instrument). In a particular embodiment, material 204 is a braided material that covers cable 202 in the area that does not make contact with a capstan surface. Instead, the higher-friction cable 202 contacts the capstan surface. In this embodiment, cable 202 is manufactured using Kevlar® or PBO, and material 204 is manufactured using HDPE, such as Dyneema®. In an alternate embodiment, cable 202 is manufactured using Dyneema® and material 204 is manufactured using Kevlar® or PBO. In this alternate embodiment, the portion of the cable covered with material 204 contacts the capstan surface. In a particular implementation, material 204 is under tension, which causes material 204 to apply pressure on cable 202. This pressure reduces the possibility of slippage between material 204 and cable 202.

Figure 3:
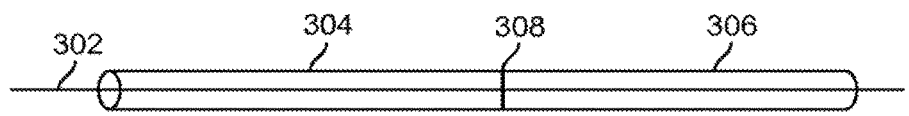
FIG. 3 depicts a cable in accordance with an embodiment of the invention covered by two different materials.

FIG. 3 depicts a cable 302 covered by a first material 304 and a second material 306 in accordance with an embodiment of the invention, where material 304 has high friction characteristics and material 306 has low friction characteristics. Materials 304 and 306 are also referred to as "covering materials". In this embodiment, material 304 contacts a capstan surface and material 306 operates or controls an end effector or other distal instrument component. Material 304 and material 306 meet at an interface point 308, which operatively couples the two materials. Materials 304 and 306 can be coupled by braiding/weaving the two materials, splicing the two materials, using a coupling element to operatively couple the materials, and so forth. In a particular embodiment, material 304 is Kevlar® or PBO, material 306 is HDPE, such as Dyneema®, and cable 302 is manufactured from a material having high strength and high elastic modulus, such as PBO.

Figure 4:
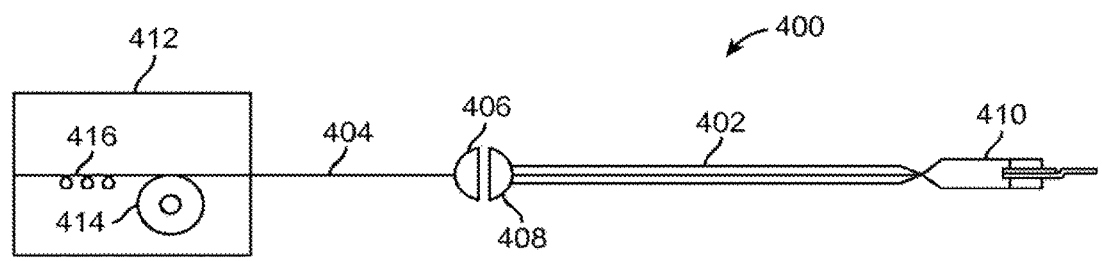
FIG. 4 depicts a surgical instrument in accordance with an embodiment of the invention that includes a cable having two portions coupled to one another.

FIG. 4 depicts a surgical instrument 400 in accordance with an embodiment of the invention that includes a cable having two portions releasably coupled to one another. The surgical instrument shown in FIG. 4 is similar to the embodiment of FIG. 1, but it includes a releasable coupling element. Surgical instrument 400 includes a first cable portion 402 (also referred to as a first tendon) having low friction properties and a second cable portion 404 (also referred to as a second tendon) having high friction properties when engaging a capstan surface. In a particular embodiment, cable portion 402 is manufactured using a synthetic polymer, such as Dyneema®. In that embodiment, cable portion 404 is manufactured using a different synthetic material having a higher coefficient of friction. Example materials for cable portion 404 include an aramid polymer (such as Kevlar®) or PBO.

Cable portion 402 has a coupling element 408 connected at a proximal end thereof. Cable portion 404 has a coupling element 406 connected at a distal end thereof. Coupling elements 406 and 408 operatively couple cable portions 402 and 404, and they are configured to releasably engage with one another. As discussed herein, coupling elements 406 and 408 apply movement and forces on cable portion 404 to cable portion 402, and vice versa. Coupling elements 406 and 408 are securely mounted or otherwise connected to cable portions 404 and 402, respectively.

The distal end of cable portion 402 is connected to an end effector 410, which can perform various surgical procedures, such as cutting, removal or destruction of tissue, insertion of medical devices, cauterization, vessel sealing, suturing, and the like. In the embodiment of FIG. 4, the low friction properties of cable portion 402 provide desirable control of the end effector by generally avoiding stick-slip motion with reference to other instrument components as cable portion 402 extends through the instrument. In a particular implementation, cable portion 402 includes a lubricated tendon passing through a sheath, as discussed below with respect to FIG. 9.

The distal end of cable portion 404 is connected to a backend mechanism 412, which includes a capstan 414 and a tension spring 416. Alternate embodiments may use any type of tension mechanism in place of tension spring 416, such as a torsion spring driving a second take-up capstan to which the end of cable portion 404 is terminated. In this alternate embodiment, the take-up capstan may be shaped to linearize the torsion spring. Cable portion 404 wraps around capstan 414 and is held in place by the friction between cable portion 404 and the surface of capstan 414. The tension spring 416 maintains tension on cable portion 404. In the described embodiment, capstan 414 is a powered capstan, as discussed below with respect to FIGS. 7A and 7B. A particular implementation of surgical instrument 400 includes a single backend mechanism 412 having multiple capstans 414 connected to multiple cable portions 404, which are then coupled (via multiple coupling elements 406 and 408) to multiple cable portions 402 and corresponding multiple end effectors 410. In this implementation, multiple cable portions 402 are bundled and routed through a single main tube.

The releasable coupling between cable portions 402 and 404 permits the simple and easy replacement of cable portion 402. In particular implementations, cable portion 402 is replaced after a particular number of surgical procedures or a particular time period. This replacement allows cable portion 402, which may be subject to relatively higher wear than cable portion 404, to be replaced, thereby reducing overall instrument cost for the effective life of the instrument. Offering a quick-release coupling between cable portions 402 and 404 facilitates this replacement. Additionally, the releasable coupling between cable portions 402 and 404 isolates any lubricant used in cable portion 402 from cable portion 404, which maintains the desired higher friction between cable portion 404 and capstan 414. As discussed below, certain embodiments of cable portion 402 use a tendon routed through a sheath such that a lubricant is located between the tendon and the sheath. The lubricant maintains a low friction in the cable portion 402, which is desirable for control of the end effector. However, such lubrication of cable portion 404 is not desirable due to a potential of reduced friction between the cable and the capstan surface. Thus, the coupling between cable portions 402 and 404 helps maintain the proper operation of surgical instrument 400 by isolating the lubricant in cable portion 402, where it is desirable for operation of the surgical instrument.

Figure 5:
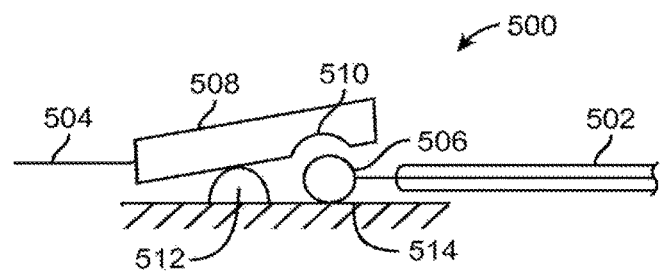
FIG. 5 depicts a coupling mechanism in accordance with an embodiment of the invention that releasably couples two cable portions.

FIG. 5 depicts a coupling mechanism 500 in accordance with an embodiment of the invention that releasably couples two cable portions. Coupling mechanism 500 is an alternative to the releasable coupling elements 406 and 408 discussed above with respect to FIG. 4. A first cable portion 502 has a ball 506 attached to the proximate end thereof. A second cable portion 504 has an arm 508 attached to the proximate end thereof. Arm 508 includes a recessed portion 510 that corresponds in shape to the outer surface of ball 506. Arm 508 slidably engages a cam 512 that allows arm 508 to rotate about cam 512 when engaging ball 506. For example, as ball 506 slides between arm 508 and surface 514, arm 508 rotates about cam 512 to allow ball 506 to continue sliding toward recessed portion 510. As ball 506 aligns with recessed portion 510, arm 508 rotates back toward a position that is substantially parallel with surface 514, thereby engaging ball 506 in recessed portion 510. Once ball 506 and arm 508 are engaged, movement of second cable portion 504 causes a corresponding movement in first cable portion 502 via arm 508 and ball 506. First cable portion 502 can be released from second cable portion 504 by rotating arm 508 to disengage ball 506, thereby allowing ball 506 to be slidably released from arm 508.

Figure 6:
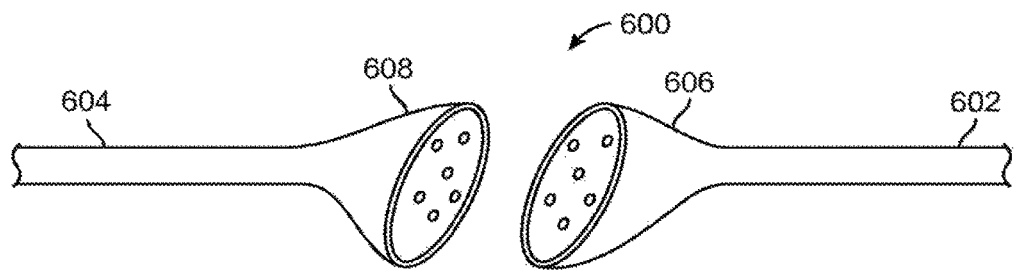
FIG. 6 depicts a coupling mechanism in accordance with another embodiment of the invention that releasably couples multiple tendons in a flexible device.

FIG. 6 depicts a coupling mechanism 600 in accordance with another embodiment of the invention that releasably couples multiple tendons in a flexible device. Coupling mechanism 600 is utilized to couple a first cable portion 602 to a second cable portion 604. As discussed herein, cable portion 604 is coupled to a capstan or other actuating mechanism that moves cable portion 604. Multiple tendons extend through cable portions 602 and 604. Coupling mechanism 600 includes a first coupling element 606 connected to cable portion 602, and a second coupling element 608 connected to cable portion 604. In the example of FIG. 6, the coupling mechanism 600 supports six tendons bundled together in a single tube or similar structure. The multiple tendons are bundled into a single main tube represented by cable portion 602. The distal ends of the multiple tendons are each connected to an end effector.

FIG. 6 illustrates a particular coupling mechanism. Alternate embodiments may utilize any type of coupling mechanism that couples multiple tendons in a flexible device.

The coupling mechanisms shown in FIGS. 4, 5, and 6 represent three examples of mechanisms to releasably couple a first cable portion to a second cable portion. Alternate embodiments may include any type of coupling mechanism that allows the interaction between the first and second cable portions as discussed herein. Further, alternate embodiments may include any type of material and any configuration or arrangement of components. Additional aspects of cable coupling mechanisms are disclosed in U.S. patent application Ser. No. 12/425,272 (filed Apr. 16, 2009; entitled "Tendon-Driven Endoscope and Method of Use"; published as U.S. Patent Application Pub. No. US 2010/0094088 A1) and U.S. patent application Ser. No. 10/988,212 (filed Nov. 12, 2004; entitled "Connector Device for a Controllable Instrument"; published as U.S. Patent Application Pub. No. 2006/0052664 A1), both of which are incorporated herein by reference.

Figure 7A:
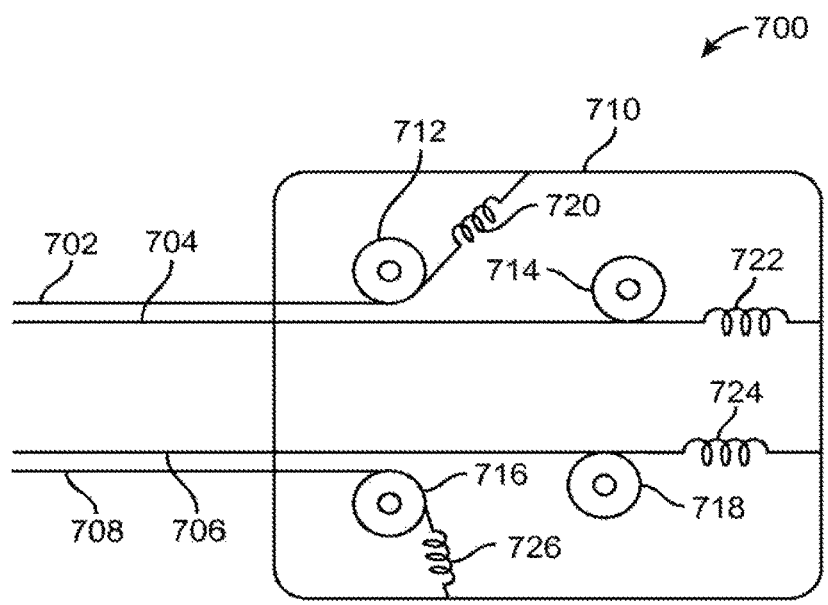
FIGS. 7A and 7B depict a portion of a surgical instrument in accordance with an embodiment of the invention using springs and capstan friction to maintain tension on tendons in the instrument.
Figure 7B:
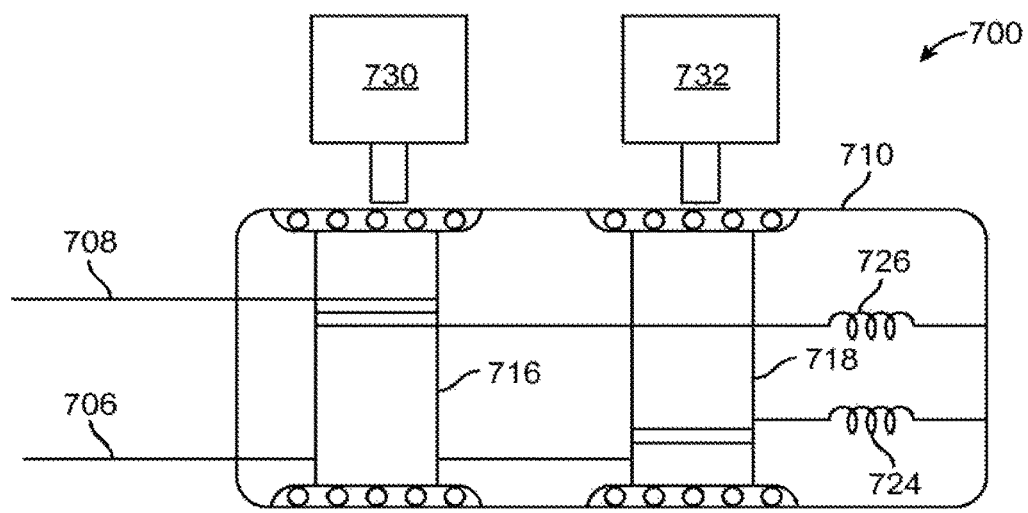

FIGS. 7A and 7B depict a portion of a surgical instrument 700 using springs and capstan friction to maintain tension on tendons in the instrument in accordance with an embodiment of the invention. FIG. 7A illustrates a top view of backend mechanism 710 connected to four cable portions 702, 704, 706, and 708 (also referred to as "tendons"). Backend mechanism 710 includes four capstans 712, 714, 716, and 718, each of which is engaged with one of the four cable portions 702-708. Cable portions 702-708 apply forces through a coupling and another cable portion to manipulate an end effector (not shown), as described above. Cable portions 702-708 are engaged with capstans 712-718 by wrapping each of the cable portions around a particular capstan, such that the resulting friction between the cable portions and the capstan surfaces maintains the engagement to provide an effective actuating pull force to the cable sufficient to operate the associated distal end component.

Backend mechanism 710 also includes tension springs 720, 722, 724, and 726 that are attached to the ends of cable portions 702-708, respectively, to maintain tension on cable portions 702-708. Springs 720-726 are biased (e.g., stretched) to apply a non-zero force to cable portions 702-708. In alternate embodiments, the springs used in backend mechanism 710 are rotary coil springs, leaf springs, or compliant members, such as bending beams, cantilever beams, or elastic bands. Other embodiments utilize a torsion spring driving a second take-up capstan. In these embodiments, the take-up capstan may be shaped to linearize the torsion spring.

FIG. 7B illustrates a side view of backend mechanism 710 and two drive motors 730 and 732 that engage with the capstans in the backend mechanism. Drive motors 730 and 732 are under the active control of human input and software executed in a teleoperated surgical system. FIG. 7B illustrates drive motors 730 and 732 that are coupled to capstans 716 and 718, respectively. When activated, drive motors 730 and 732 apply a rotational force to capstans 716 and 718, which in turn apply that force to cable portions 708 and 706 to retract the cable or relax the cable depending on the direction of rotation.

Figure 8:
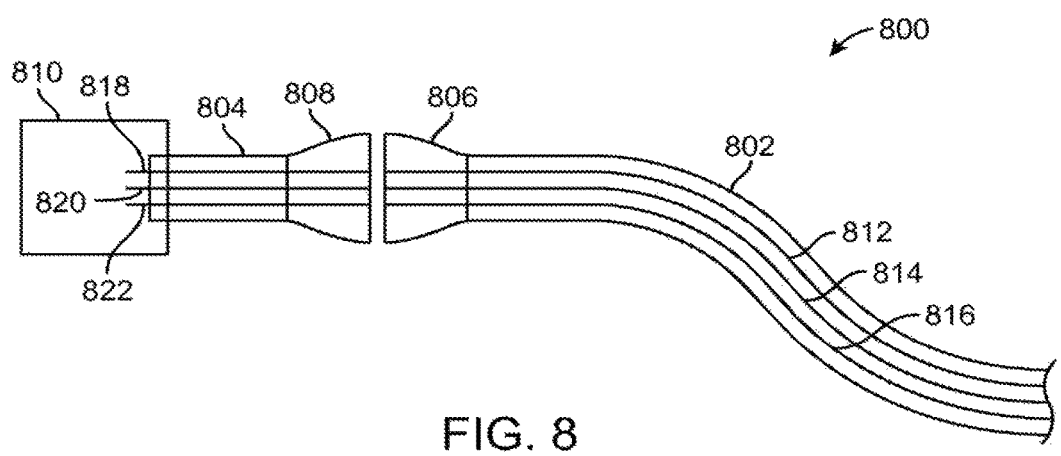
FIG. 8 depicts a portion of a flexible surgical instrument in accordance with an embodiment of the invention using a coupling mechanism that releasably couples two instrument portions having multiple tendons.

FIG. 8 depicts a portion of a flexible surgical instrument 800 in accordance with an embodiment of the invention using a coupling mechanism that releasably couples two instrument portions having multiple tendons extending therethrough. In alternate embodiments, instrument 800 includes a non-releasable coupling element, such as coupling element 106 shown in FIG. 1. Instrument 800 is capable of bending into various shapes as may result during a medical procedure when the instrument follows a curved path inside a patient to a site where a surgical procedure (or other medical or diagnostic procedure) may be performed. The path to the site may extend through an incision or through a natural orifice of a patient and along a natural lumen, such as a portion of the digestive tract of a patient. Portions of instrument 800 may further pass through an incision in the wall of the natural lumen to access the surgical site or further portions of the path that the distal end of the instrument must follow. Instrument 800 will generally have a different shape during different procedures and may need to follow a convoluted path including one or more bends.

Instrument 800 includes a first instrument portion 802 and a second instrument portion 804 coupled to one another via coupling elements 806 and 808. Coupling element 806 is connected to the proximate end of first instrument portion 802. One or more end effectors (not shown) are connected to the distal end of first instrument portion 802. Coupling element 808 is connected to the proximate end of second instrument portion 804. A backend mechanism 810 is connected to the distal end of second instrument portion 804. Coupling elements 806 and 808 may be of the type described above in FIG. 6 or any other appropriate coupling mechanism.

First instrument portion 802 includes three tendons 812, 814, and 816 positioned therein. Tendons 812, 814, and 816 are flexible tendons capable of flexing and bending as first instrument portion 802 is moved and flexed as a result of various manipulations and procedures. Tendons 812, 814, and 816 interact with a corresponding three tendons 818, 820, and 822 positioned in the relatively more proximal second instrument portion 804. In the embodiment of FIG. 8, tendons 812, 814, and 816 are manufactured using a first type of material, and tendons 818, 820, and 822 are manufactured using a second type of material. For example, as discussed above, tendons 812, 814, and 816 are manufactured using Dyneema®, and tendons 818, 820, and 822 are manufactured using Kevlar® or PBO. In this example, tendons 812, 814, and 816 are each surrounded by a stainless steel sheath of the type discussed below with respect to FIG. 9.

In specific implementations, the Dyneema® cable has a diameter of approximately 0.5 millimeter and has a desired coefficient of friction less than 0.10 between the cable and the sheath. Particular embodiments have a desired coefficient of friction in the range of 0.03-0.05 between the cable and the sheath. The Kevlar® or PBO material has a diameter of approximately 0.5 millimeter and has a desired coefficient of friction in the range of 0.30-0.50 between the cable and the surface of the capstan.

Although FIG. 8 illustrates three tendons positioned within first instrument portion 802 and second instrument portion 804, alternate embodiments may include any number of tendons positioned within the first and second instrument portions. In a specific implementation, one or more of the tendons are used to articulate intermediate sections of the instrument. The number of tendons contained in a particular flexible surgical instrument depends, in part, on the control and/or motion requirements of the end effector connected to the flexible surgical instrument. In particular embodiments, the end effector can perform a variety of functions and includes a wrist mechanism and/or a grasping mechanism. It should also be understood that the depicted first and second instrument portions are illustrative, and the combined first and second instrument portions do not necessarily have to encompass the entire instrument length. One or more additional lengthwise instrument components may be placed between and/or beyond ends of the depicted and described first and second instrument portions.

Figure 9:
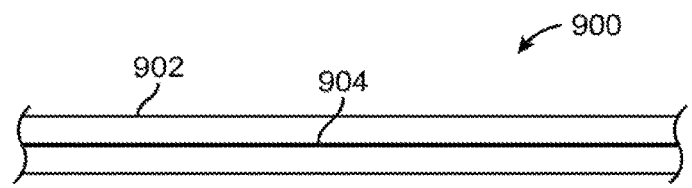
FIG. 9 depicts a portion of a flexible cable using a sheath and a tendon passing through the sheath.

FIG. 9 depicts a portion of a flexible cable 900 having a sheath 902 and a tendon 904 passing through the sheath. The portion shown in FIG. 9 is part of the first, more distal, instrument portion discussed herein; i.e., the instrument portion with an end effector at the distal end and a coupling element at the proximate end. Cable 900 may contain air or a lubricant to reduce the friction associated with movement of tendon 902 through cable 900. As discussed herein, a particular embodiment of cable 900 includes tendon 904 manufactured using HDPE, such as Dyneema®, and sheath 902 manufactured using stainless steel. Specific embodiments use a lubricant that is a mixture of water, a fatty acid or refined mineral oil, and a suitable surfactant to reduce friction in cable 900. Sheath 902 may be porous to permit movement of the lubricant between the interior and exterior of the sheath. In certain embodiments, seals such as O-rings or bellows-type seals can keep the lubricant within a sealed portion of sheath 902. Additional tendon lubrication information is disclosed in U.S. patent applications Ser. Nos. 12/346,402 (filed Dec. 30, 2008; entitled "Surgical Instrument with Sheathed Tendons"; published as U.S. Patent Application Pub. No. US 2010/0168510 A1) and 12/346,461 (filed Dec. 30, 2008; entitled "Lubricating Tendons in a Tendon-Actuated Surgical Instrument"; published as U.S. Patent Application Pub. No. US 2010/0168721 A1), both of which are incorporated herein by reference.

The described combination of sheath 902 material and tendon 904 material, as well as any lubricant, provides low friction and generally avoids stick-slip motion. In other embodiments, different metals or high strength polymers can be substituted for stainless steel in sheath 902. Similarly, in other embodiments, different materials can be substituted for Dyneema® in tendon 904.

Embodiments of the systems and methods described herein relate to surgical instruments having a cable, an end effector, and a backend mechanism to operate the end effector via the cable. Certain embodiments are used in conjunction with one or more conventional surgical systems and methods. For example, one embodiment is used as an improvement of existing surgical systems.

Although the components and modules illustrated herein are shown and described in a particular arrangement, the arrangement of components and modules may be altered to implement surgical instruments in a different manner, or to manipulate surgical systems in a different manner. In other embodiments, one or more additional components or modules may be added to the described systems, and one or more components or modules may be removed from the described systems. Alternate embodiments may combine two or more of the described components or modules into a single component or module.

Although specific embodiments of the invention have been described and illustrated, the invention is not to be limited to the specific forms or arrangements of parts so described and illustrated. The scope of the invention is to be defined by the claims appended hereto and their equivalents.

The invention claimed is:

1. A surgical device comprising:
a first cable portion that includes an inner material and a first covering material that extends over the inner material, wherein the first covering material is configured such that when a first component is engaged, a first friction exists between the first cable portion and the first component; and
a second cable portion that includes the inner material and a second covering material that extends over the inner material and having a first end operatively coupled to a first end of the first cable portion, wherein:
the first cable portion is free of the second covering material,
the second cable portion is free of the first covering material,
the second covering material is configured such that when the second cable portion engages a second component, a second friction exists between the second cable portion and the second component,
the first covering material of the first cable portion has a first exterior surface containing a first material with a first friction characteristic that is independent of engagement with the first component, and
the second covering material of the second cable portion has a second exterior surface containing a second material that is different from the first material with a second friction characteristic that is independent of engagement with the second component such that the second friction characteristic is greater than the first friction characteristic and the second friction is greater than the first friction.

2. The surgical device of claim 1, wherein the first cable portion includes a sheath configured to facilitate passage of the inner material and the first covering material of the first cable portion.

3. The surgical device of claim 2, wherein the first covering material comprises high density polyethylene.

4. The surgical device of claim 2, wherein the sheath comprises stainless steel.

5. The surgical device of claim 1, wherein the second cable portion comprises an aramid polymer.

6. The surgical device of claim 1, wherein the second cable portion comprises poly(p-phenylene-2,6-benzobisoxazole).

7. A surgical device comprising:
a first cable portion engaging a first component such that a first friction exists between the first cable portion and the first component, wherein the first cable portion has an exterior surface that contains a first material that has a first coefficient of friction;
a first coupling element operatively coupled to the first cable portion such that the first material extends to the first coupling element;
a second coupling element configured to releasably physically couple to the first coupling element; and
a second cable portion having a first end operatively coupled to the second coupling element, the second cable portion engaging a second component such that a second friction exists between the second cable portion and the second component, wherein:
the second friction is greater than the first friction;
the second cable portion has an exterior surface that contains a second material that is different than the first material and that has a second coefficient of friction that is greater than the first coefficient of friction; and
the second material extends to the second coupling element.

8. The surgical device of claim 1, wherein the first cable portion is configured to be connected to an end effector.

9. The surgical device of claim 1, wherein the second component is a powered capstan.

10. The surgical device of claim 1, wherein the first friction has an associated coefficient of friction less than 0.10.

11. The surgical device of claim 1, wherein the second friction has an associated coefficient of friction greater than 0.3.

12. The surgical device of claim 1, wherein the first cable portion is operatively joined to the second cable portion along a common lengthwise axis defined through the first and second cable portions.

13. The surgical device of claim 1, wherein the first covering material is a braided covering material.

14. The surgical device of claim 1, wherein the first covering material is under tension and applies pressure to the inner material.

15. The surgical device of claim 1, wherein the first covering material is directly physically coupled to the second covering material.

* * * * *